United States Patent [19]
Johnson et al.

[11] Patent Number: 6,017,850
[45] Date of Patent: Jan. 25, 2000

[54] HERBICIDAL COMPOSITION AND METHOD OF WEED CONTROL

[75] Inventors: Michael Donald Johnson; Cheryl Lynn Dunne, both of Vero Beach, Fla.; Manfred Hudetz, Rheinfelden, Switzerland; Daniel Worden Kidder, Kernersville, N.C.

[73] Assignee: Novartis Finance Corporation, New York, N.Y.

[21] Appl. No.: 08/759,699

[22] Filed: Dec. 6, 1996

[51] Int. Cl.[7] .......................... A01N 43/00; A01N 43/40; A01N 43/64; A01N 43/54; A01N 43/02
[52] U.S. Cl. .......................... 504/124; 504/129; 504/130; 504/134; 504/135; 504/136; 504/140
[58] Field of Search .................................... 504/127, 214, 504/124, 129, 130, 134, 135, 136, 140

[56] References Cited

U.S. PATENT DOCUMENTS

| | | | |
|---|---|---|---|
| 5,512,534 | 4/1996 | Frisch et al. | 504/103 |
| 5,596,124 | 1/1997 | Cary et al. | 560/61 |
| 5,736,486 | 4/1998 | Pappas-Fader et al. | 504/127 |
| 5,834,006 | 11/1998 | Smith et al. | 424/409 |

*Primary Examiner*—Shelley A. Dodson
*Assistant Examiner*—Alton Pryor
*Attorney, Agent, or Firm*—William A. Teoli, Jr.; John D. Peabody, III

[57] ABSTRACT

A herbicidal composition comprising, in addition to customary inert formulation adjuvants, as active ingredient a) an antagonistically active amount of at least one compound A selected from the group of compounds of formula $A_1$ $$U-SO_2-NH-CO-NH-\underset{\underset{R_2}{\overset{N}{\|}}}{\overset{N}{\underset{}{\bigvee}}}\overset{R_1}{\underset{E}{}} \qquad (A_1)$$

and compounds of formula $A_2$ $$(A_2)$$

compounds of formula $A_3$ $$(A_3)$$

b) a herbicidally effective amount of at least one compound G selected from the group of compounds, preferably having the 2R-configuration, of formula $G_1$ $$W-O-\bigcirc-O-\overset{CH_3}{\underset{*}{\overset{|}{C}H}}-COO-R_{10}, \qquad (G_1)$$

compounds of formula $G_2$ $$(G_2)$$

c) an acid the pK value of which is smaller than the pK values of compounds G and A.

14 Claims, No Drawings

HERBICIDAL COMPOSITION AND METHOD OF WEED CONTROL

The present invention relates to a novel herbicidal composition comprising a herbicidal active ingredient combination suitable for the selective control of weeds in crops of useful plants, for example in crops of cereals, rice, cotton, rape, sorghum, sugar cane, sugar beet, sunflowers, vegetables, plantation crops, fodder plants and especially maize and soybeans.

The invention relates also to a method of controlling weeds in crops of useful plants, and the use of the novel composition for that purpose.

The following compounds A, selected from the group of compounds of formula $A_1$

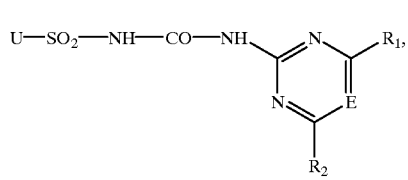
(A$_1$)

wherein
$R_1$ is $CH_3$, $OCH_3$, $OCHF_2$ or Cl,
$R_2$ is $CH_3$, $OCH_3$, $OCHF_2$ or $CF_3$,
E is CH or N, and
U is a radical of the formula

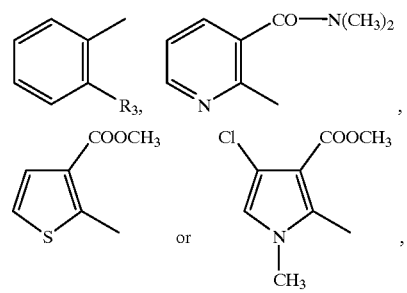

wherein
$R_3$ is $CH_2CH_2CF_3$, $CF_3$ or $COOR_4$, and
$R_4$ is $CH_3$, $CH_2CH_3$ or a radical of the

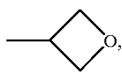

and their agrochemically acceptable salts, and compounds of formula $A_2$

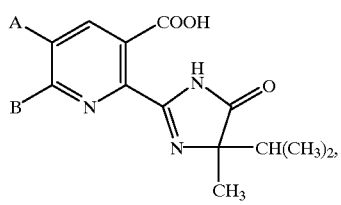
(A$_2$)

wherein
A is hydrogen,
B is $CH_2CH_3$ or $CH_2OCH_3$, or

A together with B forms a radical of the formula —CH═CH—CH═CH—, and their agrochemically acceptable salts, and compounds of formula $A_3$

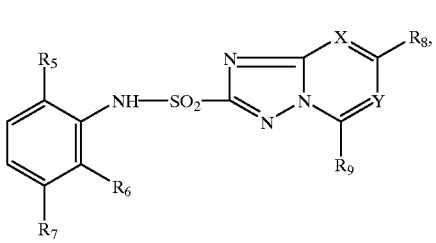
(A$_3$)

wherein
$R_5$ is F, Cl or $COOCH_3$,
$R_6$ is F or Cl,
$R_7$ is hydrogen or $CH_3$,
$R_8$ is $CH_3$, $OCH_3$ or F,
$R_9$ is hydrogen, $OCH_3$ or $OCH_2CH_3$, and
X and Y are each independently of the other CH or N, one of X and Y always being N, and their agrochemically acceptable salts, are known as herbicides, for example, from U.S. Pat. No. 4,394,506, U.S. Pat. No. 4,789,393, EP 469,460, Proc. N. Cent. Weed Control Conf., 1985, 39, 1220; U.S. Pat. No. 4,478,635, U.S. Pat. No. 4,443,245 and U.S. Pat. No. 5,209,771.

The compounds G selected from the group of compounds, preferably having the 2R-configuration, of formula $G_1$

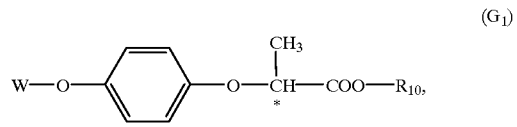
(G$_1$)

wherein
$R_{10}$ is $C_1$–$C_4$alkyl, $CH_2C\equiv CH$ or $CH_2CH_2O$—N═C$(CH_3)_2$,
W is a radical of the formula

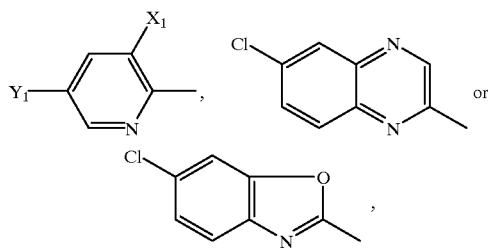

wherein
$X_1$ is hydrogen or F and
$Y_1$ is Cl or $CF_3$, and
their agrochemically acceptable salts, and compounds of formula $G_2$

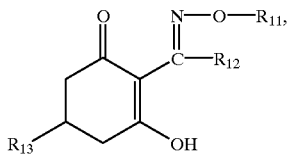

wherein
$R_{11}$, is $CH_2CH_3$ or —$CH_2$—$CH$=$CH$—$Cl$ (trans),
$R_{12}$ is $CH_2CH_3$ or $CH_2CH_2CH_3$ and
$R_{13}$ is a radical of the formula

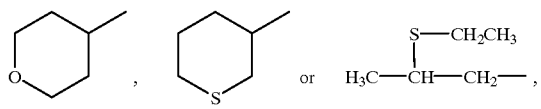

and
their agrochemically acceptable salts, have herbicidal activity, especially against grasses, and are described, for example, in U.S. Pat. No. 4,435,207, U.S. Pat. No. 4,505,743, U.S. Pat. No. 4,687,849, Proc. Br. Crop Prot. Conf.-Weeds, 1982,1,11, U.S. Pat. No. 4,249,937, GB 2090246 and U.S. Pat. No. 4,422,864.

It has now been found that when mixtures of compounds G with compounds A are used for weed control, the herbicidal activity of the compounds G, especially against grasses, is reduced by the compounds A. However, it has been found, surprisingly, that the antagonism brought about by the compounds A can be substantially reduced by the addition of certain acids.

According to the present invention there is therefore proposed a novel herbicidal composition for the selective control of weeds comprising, in addition to customary inert formulation adjuvants, as active ingredient a) an antagonistically active amount of at least one compound A selected from the group of compounds of formula $A_1$

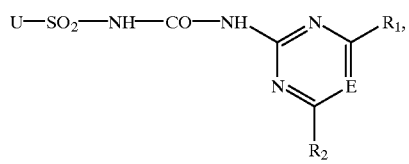

wherein
$R_1$ is $CH_3$, $OCH_3$, $OCHF_2$ or $Cl$,
$R_2$ is $CH_3$, $OCH_3$, $OCHF_2$ or $CF_3$,
E is CH or N, and
U is a radical of the formula

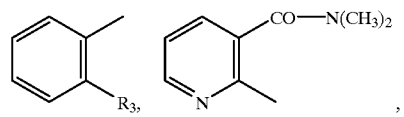

-continued

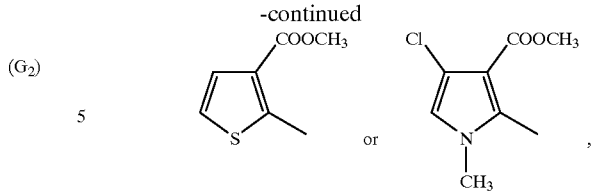

wherein
$R_3$ is $CH_2CH_2CF_3$, $CF_3$ or $COOR_4$, and
$R_4$ is $CH_3$, $CH_2CH_3$ or a radical of the formula

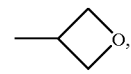

and
their agrochemically acceptable salts, and
compounds of formula $A_2$

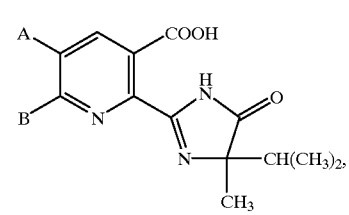

wherein
A is hydrogen,
B is $CH_2CH_3$ or $CH_2OCH_3$, or
A together with B forms a radical of the formula
—CH=CH—CH=CH—, and
their agrochemically acceptable salts, and
compounds of formula $A_3$

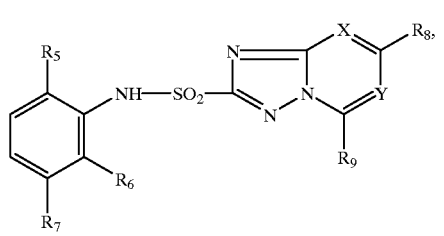

wherein
$R_5$ is F, Cl or $COOCH_3$,
$R_6$ is F or Cl,
$R_7$ is hydrogen or $CH_3$,
$R_8$ is $CH_3$, $OCH_3$ or F,
$R_9$ is hydrogen, $OCH_3$ or $OCH_2CH_3$, and
X and Y are each independently of the other CH or N, one of X and Y always being N, and their agrochemically acceptable salts, b) a herbicidally effective amount of at least one compound G selected from the group of compounds, preferably having the 2R-configuration, of formula $G_1$

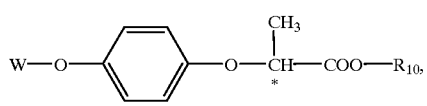

wherein
$R_{10}$ is $C_1$–$C_4$alkyl, $CH_2C{\equiv}CH$ or $CH_2CH_2O{-}N{=}C(CH_3)_2$,
W is a radical of the formula

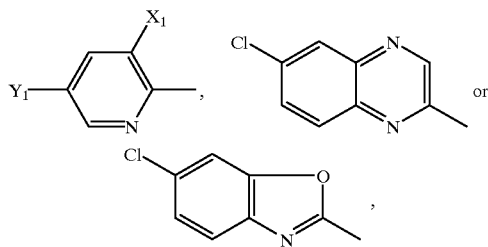

wherein
$X_1$ is hydrogen or F and
$Y_1$ is Cl or $CF_3$, and
their agrochemically acceptable salts, and
compounds of formula $G_2$

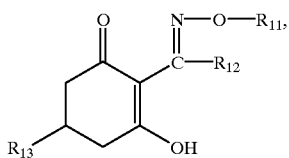

wherein
$R_{11}$ is $CH_2CH_3$ or $-CH_2-CH{=}CH-Cl$ (trans),
$R_{12}$ is $CH_2CH_3$ or $CH_2CH_2CH_3$ and
$R_{13}$ is a radical of the formula

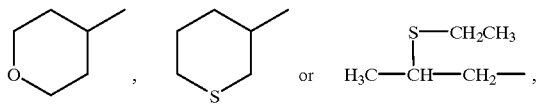

and
their agrochemically acceptable salts, and
c) an acid the pK value of which is smaller than the pK values of compounds G and A.

It is highly surprising that the addition of the acid c) substantially reduces the previously observed antagonistic action of compounds A against compounds G, since it is known from EP-A-512,739 that the presence of an acid in a herbicidal mixture of sulfonamide or sulfonylurea herbicides and cationic surfactants reduces the phytotoxicity, that is to say the herbicidal activity, of the mixture. In that respect, therefore, according to the present invention the opposite effect is achieved: the herbicidal activity of the composition comprising compounds G and A is increased by the addition of acid.

Acids suitable for use in the compositions according to the invention are basically any chemical compounds the pK value of which is smaller than the pK values of compounds G and A and which do not impair the activity of compounds G and A in any way, for example by decomposition. It is possible to use mono- or poly-valent inorganic or organic acids, especially carboxylic acids, which may be unsubstituted or substituted, for example by alkyl, phenyl, hydroxy or by halogen. Preferred acids are hydrochloric acid, sulfuric acid, nitric acid, phosphoric acids, formic acid and acetic acid, also oxalic, malonic and succinic acid, and also lactic acid, preferably phosphoric acid and citric acid, and especially phthalic acid. It is also possible for mixtures of such acids to be used. Instead of the pure acids it is also possible to use corresponding buffer solutions.

The acid is preferably used in an amount that adjusts the pH value of the composition to a value of from 3 to 6, especially from 4 to 5.

The Application relates also to the use of the acid c) for increasing the effectiveness of herbicidal compositions comprising compounds G and A.

The herbicidal compositions according to the invention can be used against a large number of agronomically important weeds, such as Stellaria, Nasturtium, Agrostis, Avena, Sinapis, Lolium, Solanum, Phaseolus, Echinochloa, Scirpus, Monochoria, Sagittaria, Bromus, Alopecurus, Sorghum halepense or bicolor, Rottboellia, Cyperus, Abutilon, Sida, Xanthium, Amaranthus, Chenopodium, Ipomoea, Chrysanthemum, Galium, Viola, Veronica and especially Digitaria, Setaria and Eriochloa.

The composition according to the invention is suitable for all methods of application customary in agriculture, for example preemergence application, postemergence application and seed dressing. It is suitable for the control of weeds in crops of useful plants, such as cereals, rice, cotton, rape, sorghum, sugar cane, sugar beet, sunflowers, vegetables, plantation crops, fodder plants and especially maize and soybeans, and also for the non-selective control of weeds.

Crops are to be understood as including those which have been rendered tolerant to herbicides or classes of herbicide by conventional methods of breeding or genetic engineering.

The composition according to the invention comprises active ingredient G and active ingredient A in any mixture ratio, but generally has an excess of one component over the other. Preferred mixture ratios of active ingredient G and mixing partner A are 50:1 and preferably 20:1.

Preferred herbicidal compositions according to the present invention comprise at least one compound G selected from the group of compounds of formula $G_1$

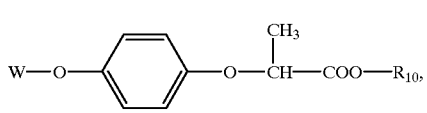

wherein
$R_{10}$ is $C_1$–$C_4$alkyl,
W is a radical of the formula

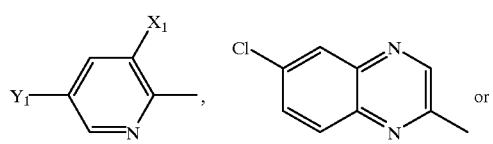

-continued

[Structure: 6-chloro-2-methylbenzoxazole]

wherein $X_1$ is hydrogen and $Y_1$ is $CF_3$, and their D-enantiomers and agrochemically acceptable salts, and compounds of formula $G_2$ $(G_2)$

[Structure of $G_2$]

wherein $R_{10}$ is $CH_2CH_3$ or $-CH_2-CH=CH-Cl$ (trans), $R_{12}$ is $CH_2CH_3$ or $CH_2CH_2CH_3$ and $R_{13}$ is a radical of the formula $$H_3C-CH(S-CH_2CH_3)-CH_2-,$$

and their agrochemically acceptable salts.

Herbicidal compositions that have proved especially effective are those comprising at least one compound A selected from the group of compounds of formula $A_1$ $(A_1)$ $$U-SO_2-NH-CO-NH-\text{[triazine with }R_1, R_2, E\text{]}$$

wherein $R_1$ is $CH_3$ or Cl, $R_2$ is $CH_3$ or $OCH_3$,

E is CH, and

U is a radical of the formula

[Structure: o-tolyl with $R_3$]

wherein $R_3$ is $COOR_4$, and $R_4$ is $CH_2CH_3$ or a radical of the formula

[Structure: methyloxetane]

and their agrochemically acceptable salts, and compounds of formula $A_2$ $(A_2)$

[Structure of $A_2$ with A, B, COOH, $CH(CH_3)_2$, $CH_3$]

wherein

A together with B forms a radical of the formula $-CH=CH-CH=CH-$, and their agrochemically acceptable salts, and compounds of formula $A_3$ $(A_3)$

[Structure of $A_3$ with $R_5, R_6, R_7, R_8, R_9, X, Y$]

wherein $R_5$ is $COOCH_3$, $R_6$ is Cl, $R_7$ is hydrogen, $R_8$ is F, $R_9$ is $OCH_2CH_3$, and X and Y are each independently of the other CH or N, one of X and Y always being N, and their agrochemically acceptable salts.

Preferred compounds G for use in the compositions according to the invention are haloxyfop, clodinafop, propaquizafop, quizalofop-P, fluazifop-P, fenoxaprop and mixtures of fenoxaprop and fluazifop-P; and also sethoxydim, clethodim, cloproxydim, caloxydim and cycloxydim.

Preferably the compounds A are oxasulfuron, chlorimuron, thifensulfuron, nicosulfuron, primisulfuron, prosulfuron, halosulfuron or a mixture of primisulfuron and prosulfuron; and also imazamox, imazethapyr, imazaquin, diclosulam, flumetsulam, metosulam and chloransulam.

Preferred combinations of compounds G and A include mixtures of quizalafop-P, fluazifop-P, fenoxaprop mixed with fluazifop-P; sethoxydim and also clethodim as compounds G in each case in combination with one of the following compounds A oxasulfuron, chloransulam and chlorimuron.

The above-mentioned active ingredients are known from the The Pesticide Manual, Tenth Edition; BCPC, 1994. Oxasulfuron is mentioned in AGROW No 245, 1st December 1995, p. 20; diclosulam and cloransulam in AGROW No 261, 2nd August 1996, p. 21, and imazamox in AGROW No 261, 2nd August 1996, p. 23. Caloxydim is described in AGROprojects: W0046, PJB Publ. Ltd., January 1996.

The rate of application may vary within wide limits and depends upon the nature of the soil, the type of use (pre- or post-emergence; seed dressing; application to the seed furrow; no tillage application, etc.), the crop plant, the weed to be controlled, the prevailing climatic circumstances and other factors determined by type of use, time of use and the target crop. Generally the active ingredient mixture according to the invention can be applied at a rate of application of from 20 to 400, especially from 30 to 350, and more especially from 40 to 300, g/active ingredient mixture/ha.

In the composition according to the invention, component G is present in a ratio by weight with respect to component A of 50:1, especially 20:1, and more especially 3:1.

The mixtures of compound G with compound A may be used in unmodified form, that is to say as obtained in the synthesis, but they are preferably formulated in customary manner together with the adjuvants customarily employed in formulation technology, such as solvents, solid carriers or surfactants, e.g. into emulsifiable concentrates, unless compound A has been selected from compounds of formula $A_1$, directly sprayable or dilutable solutions, wettable powders, soluble powders, dusts, granules or microcapsules. As with the nature of the compositions, the methods of application, such as spraying, atomising, dusting, wetting, scattering or pouring, are chosen in accordance with the intended objectives and the prevailing circumstances.

The formulations, that is to say the compositions, preparations or mixtures comprising the compounds (active ingredients) G and A and, as appropriate, one or more solid or liquid formulation adjuvants, are prepared in a manner known per se, e.g. by homogeneously mixing and/or grinding the active ingredients with the formulation adjuvants, for example solvents or solid carriers. It is also possible to use surface-active compounds (surfactants) in the preparation of the formulations.

Suitable solvents are: aromatic hydrocarbons, preferably the fractions containing 8 to 12 carbon atoms, for example xylene mixtures or substituted napthalenes; phthalic acid esters, such as dibutyl or dioctyl phthalate, aliphatic hydrocarbons, such as cyclohexane or paraffins, alcohols and glycols, and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or N,N-dimethylformamide; and vegetable oils and epoxidised vegetable oils, such as epoxidised coconut oil or soybean oil; or water.

The solid carriers used, e.g. for dusts and dispersible powders, are normally natural mineral fillers, such as calcite, talcum, kaolin, montmorillonite or attapulgite. In order to improve the physical properties of the formulation it is also possible to add highly dispersed silicic acid or highly dispersed absorbent polymers. Suitable granulated adsorptive carriers are porous types, for example pumice, broken brick, sepiolite or bentonite, and suitable non-sorbent carriers are, for example, calcite or sand. In addition, a great number of pregranulated materials of inorganic or organic nature can be used, e.g. especially dolomite or pulverised plant residues.

Depending upon the nature of the compounds to be formulated, suitable surface-active compounds are non-ionic, cationic and/or anionic surfactants and surfactant mixtures having good emulsifying, dispersing and wetting properties.

Both water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurine salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, the alkyl moiety of acyl radicals also being included, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Examples of alkylarylsulfonates are the sodium, calcium or triethanolamine salts of dodecylbenzenesulfonic acid, dibutyinaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylenelpolyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology, which may also be used in the compositions according to the invention, are described inter alia in "Mc Cutcheon's Detergents and Emulsifiers Annual", MC Publishing Corp., Ridgewood New Jersey, 1981, Stache, H., "Tensid-Taschenbuch", Carl Hanser Verlag, Munich/Vienna, 1981 and M. and J. Ash, "Encyclopedia of Surfactants", Vol I–III, Chemical Publishing Co., New York, 1980–1981.

The herbicidal formulations generally comprise from 0.1 to 99% by weight, especially from 0.1 to 95% by weight, active ingredient mixture of compound G with compound A, from 1 to 99.9% by weight of a solid or liquid formulation adjuvant and from 0 to 25% by weight, especially from 0.1 to 25% by weight, of a surfactant.

Whereas commercial products will preferably be formulated as concentrates, the end user will normally employ dilute formulations.

The compositions may also comprise further auxiliaries, such as stabilisers, e.g. vegetable oils or epoxidised vegetable oils (epoxidised coconut oil, rape oil or soybean oil), antifoams, for example silicone oil, preservatives, viscosity regulators, binders and tackifiers, as well as fertilisers or other active ingredients.

Preferred formulations have especially the following composition (throughout, percentages are by weight):

Emulsifiable concentrates:
  active ingredient mixture: 1 to 90%, preferably 5 to 20%
  surface-active agent: 1 to 30%, preferably 10 to 20%
  liquid carrier: 5 to 94%, preferably 70 to 85%

Dusts:
  active ingredient mixture: 0.1 to 10%, preferably 0.1 to 5%
  solid carrier: 99.9 to 90%, preferably 99.9 to 99%

Suspension concentrates:
  active ingredient mixture: 5 to 75%, preferably 10 to 50%
  water: 94 to 24%, preferably 88 to 30%
  surface-active agent: 1 to 40%, preferably 2 to 30%

Wettable powders:
  active ingredient mixture: 0.5 to 90%, preferably 1 to 80%
  surface-active agent: 0.5 to 20%, preferably 1 to 15%
  solid carrier: 5 to 95%, preferably 15 to 90%

Granules:
  active ingredient mixture: 0.1 to 30%, preferably 0.1 to 15%
  solid carrier: 99.5 to 70%, preferably 97 to 85%

The following Examples further illustrate, but do not limit, the invention.

Formulation Examples for mixtures of compounds G and A (throughout, percentages are by weight):

| F1. Emulsifiable concentrates | a) | b) | c) | d) |
|---|---|---|---|---|
| active ingredient mixture | 5% | 10% | 5% | 50% |
| calcium dodecyl benzene-sulfonate | 6% | 8% | 6% | 8% |
| castor oil polyglycol ether (36 mol of ethylene oxide) | 4% | — | 4% | 4% |
| octylphenol polyglycol ether (7–8 mol of ethylene oxide) | — | 4% | — | 2% |
| cyclohexanone | — | — | 10% | 20% |
| aromatic hydrocarbon mixture $C_9$–$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| aromatic hydrocarbon mixture $C_9$–$C_{12}$ | 75% | 60% | — | — |

These solutions are suitable for application in the form of microdrops.

| F3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene sulfonate | — | 6% | 5% | 6% |
| octylphenol polyglycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is thoroughly mixed with the additives and the mixture is thoroughly ground in a suitable mill, affording wettable powders which can be diluted with water to give suspensions of any desired concentration.

| F4. Coated granules | a) | b) | c) |
|---|---|---|---|
| active ingredient mixture | 0.1% | 5% | 15% |
| highly dispersed silicic acid | 0.9% | 2% | 2% |
| inorganic carrier (diameter 0.1–1 mm) for example $CaCO_3$ or $SiO_2$ | 99.0% | 93% | 83% |

The active ingredient is dissolved in methylene chloride and the solution is sprayed onto the carrier, and the solvent is subsequently evaporated off in vacuo.

| F5. Coated granules | a) | b) | c) |
|---|---|---|---|
| active ingredient mixture | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1–1 mm) for example $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient mixture | 0.1% | 1% | 5% |
| talcum | 39.9% | 49% | 35% |
| kaolin | 60.0% | 50% | 60% |

Ready-for-use dusts are obtained by mixing the active ingredient with the carriers, and grinding the mixture in a suitable mill.

| F8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

It is often more practical for the compounds G and A and the acid c) to be formulated separately and to be brought together only shortly before application in the applicator in the desired mixture ratio in the form of a "tank mixture" in water.

BIOLOGICAL EXAMPLES

Example B1

Post-emergence test:

The test plants (Glycine max., Setaria faberi, Setaria viridis, Eriochloa villosa, Digitaria sanguinalis) are raised in a greenhouse in plastics pots containing standard soil, and in the 2- to 4-leaf stage (weeds) or the 1- to 2-trifoliate leaf stage (soybeans) are sprayed with an aqueous suspension of the test compounds, corresponding to a rate of application of 150 liters water/ha, which has been adjusted to a pH value of 5 with a potassium biphthalate buffer (20.42 g of potassium biphthalate in 500 ml of water, addition of 45.2 ml of 1N sodium hydroxide solution, water to make up to 1 liter, diluted in a ratio of 1:1 to make the suspension used). The test plants are then grown on in the greenhouse under optimum conditions.

After 17 days the test is evaluated. The results obtained are shown in Tables B1 and B2. They represent the average values from three series of tests.

As expected, soybeans (Glycine max.) are virtually undamaged by the herbicides used.

The same results are obtained when compounds G and A are formulated in accordance with the above Formulation Examples.

TABLE B1

| G + A | Digitaria s. | Eriochloa v. | Setaria f. | Setaria v. |
|---|---|---|---|---|
| Assure + Expert | ++ | ++ | ++ | ++ |
| Fusilade + Expert | + | + | + | o |
| Fusion + Expert | ++ | + | + | + |
| Assure + FirstRate | + | + | o | o |
| Fusilade + FirstRate | ++ | ++ | + | + |
| Fusion + FirstRate | ++ | ++ | o | o |

TABLE B2

| G + A | Digitaria s. | Eriochloa v. | Setaria f. | Setaria v. |
|---|---|---|---|---|
| Select + Expert | ++ | ++ | ++ | ++ |
| Select + Classic | + | + | + | ++ |
| Select + FirstRate | ++ | ++ | ++ | + |

++ = increase in activity by the addition of acid is greater than or equal to 10%
+ = increase in activity by the addition of acid is less than 9%
o = no increase in activity by the addition of acid
Assure = quizalofop-P, rate of application: 54 g/ha, concentration in suspension: 0.36 g/l
Fusilade = fluazipfop-P; rate of application: 210 g/ha, concentration in suspension: 1.40 g/l
Fusion = fenoxaprop + fluazifop-P; rate of application: 186 g/ha, concentration in suspension: 1.24 g/l
Expert = oxasulfuron; rate of application: 79 g/ha, concentration in suspension: 0.53 g/l
First Rate = chloransulam-methyl; rate of application: 20 g/ha, concentration in suspension: 0.13 g/l
Select = clethodim; rate of application: 105 g/ha, concentration in suspension: 0.70 g/l
Classic = chlorimuron; rate of application: 13 g/ha, concentration in suspension: 0.09 g/l

What is claimed is:

1. A herbicidal composition comprising, in addition to customary inert formulation adjuvants, as active ingredient
    a) an antagonistically active amount of at least one compound A selected from the group of compounds of formula $A_1$

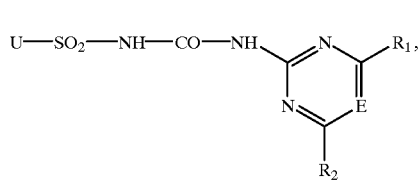

wherein
    $R_1$ is $CH_3$, $OCH_3$, $OCHF_2$ or Cl,
    $R_2$ is $CH_3$, $OCH_3$, $OCHF_2$ or $CF_3$,
    E is CH or N, and
    U is a radical of the formula

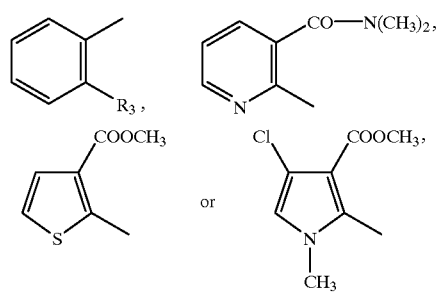

wherein

R$_3$ is CH$_2$CH$_2$CF$_3$, CF$_3$ or COOR$_4$, and

R$_4$ is CH$_3$, CH$_2$CH$_3$ or a radical of the formula

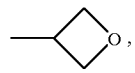

and their agrochemically acceptable salts, and compounds of formula A$_2$

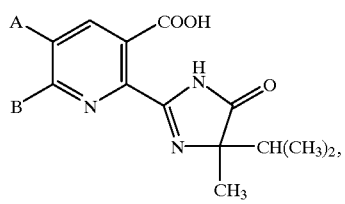 (A$_2$)

wherein

A is hydrogen,

B is CH$_2$CH$_3$ or CH$_2$OCH$_3$, or

A together with B forms a radical of the formula —CH=CH—CH=CH—, and their agrochemically acceptable salts, and compounds of formula A$_3$

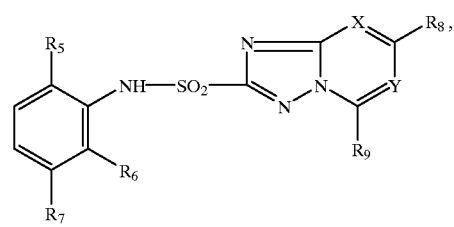 (A$_3$)

wherein

R$_5$ is F, Cl or COOCH$_3$,

R$_6$ is F or Cl,

R$_7$ is hydrogen or CH$_3$,

R$_8$ is CH$_3$, OCH$_3$ or F,

R$_9$ is hydrogen, OCH$_3$ or OCH$_2$CH$_3$, and

X and Y are each independently of the other CH or N, one of X and Y always being N, and their agrochemically acceptable salts, b) a herbicidally effective amount of at least one compound G selected from the group of compounds, of formula G$_1$

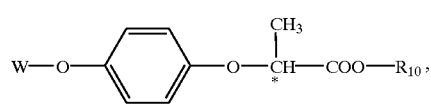 (G$_1$)

wherein

R$_{10}$ is C$_1$–C$_4$alkyl, CH$_2$C≡CH or CH$_2$CH$_2$O—N=C(CH$_3$)$_2$,

W is a radical of the formula

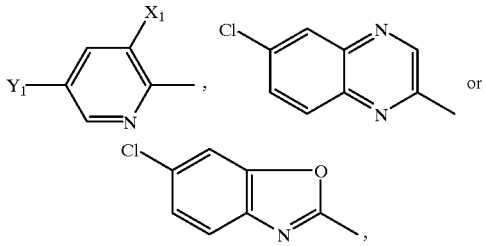

wherein

X$_1$ is hydrogen or F and

Y$_1$ is Cl or CF$_3$, and their agrochemically acceptable salts, and compounds of formula G$_2$

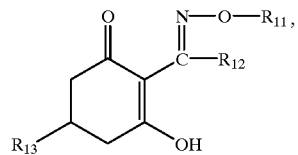 (G$_2$)

wherein

R$_{11}$ is CH$_2$CH$_3$ or —CH$_2$—CH=CH—Cl (trans),

R$_{12}$ is CH$_2$CH$_3$ or CH$_2$CH$_2$CH$_3$ and

R$_{13}$ is a radical of the formula

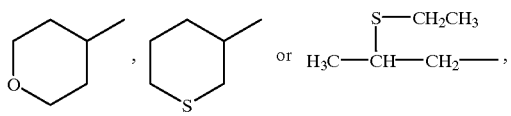

and their agrochemically acceptable salts, and c) an acid the pK value of which is smaller than the pK values of compounds G and A.

2. A herbicidal composition according to claim 1, which comprises at least one compound G selected from the group of compounds of formula G$_1$

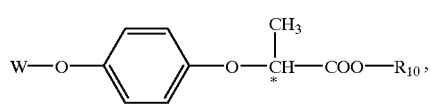 (G$_1$)

wherein $R_{10}$ is $C_1$–$C_4$alkyl,

W is a radical of the formula

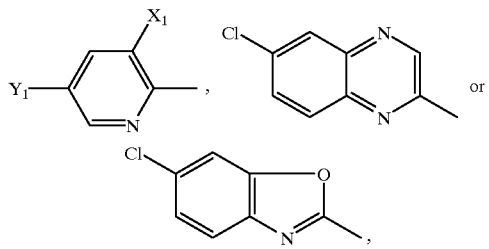

wherein $X_1$ is hydrogen and $Y_1$ is $CF_3$, and their agrochemically acceptable salts, and compounds of formula $G_2$

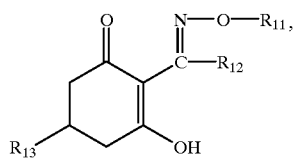

(G₂)

wherein $R_{11}$ is $CH_2CH_3$ or —$CH_2$—CH=CH—Cl (trans), $R_{12}$ is $CH_2CH_3$ or $CH_2CH_2CH_3$ and $R_{13}$ is a radical of the formula

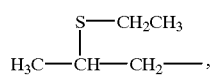

and their agrochemically acceptable salts.

3. A herbicidal composition according to claim 1, which comprises at least one compound A selected from the group of compounds of formula $A_1$

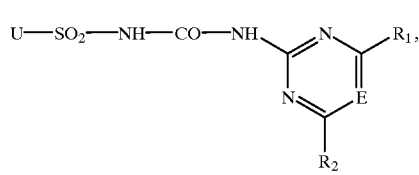

(A₁)

wherein $R_1$ is $CH_3$ or Cl, $R_2$ is $CH_3$ or $OCH_3$,

E is CH, and

U is a radical of the formula

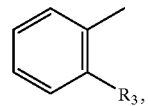

wherein $R_3$ is $COOR_4$, and $R_4$ is $CH_2CH_3$ or a radical of the formula

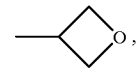

and their agrochemically acceptable salts, and compounds of formula $A_2$

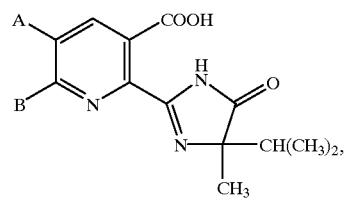

(A₂)

wherein

A together with B forms a radical of the formula —CH=CH—CH=CH—, and their agrochemically acceptable salts, and compounds of formula $A_3$

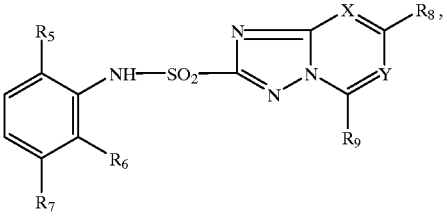

(A₃)

wherein $R_5$ is $COOCH_3$, $R_6$ is Cl, $R_7$ is hydrogen, $R_8$ is F, $R_9$ is $OCH_2CH_3$, and X and Y are each independently of the other CH or N, one of X and Y always being N, and their agrochemically acceptable salts.

4. A herbicidal composition according to claim 1, which comprises a compound G selected from quizalofop-P, fluazifop-P, fenoxaprop mixed with fluazifop-P; sethoxydim and clethodim and a compound A selected from oxasulfuron, chloransulam and chlorimuron.

5. A herbicidal composition according to claim 1, which comprises phthalic acid as component (c).

6. A herbicidal composition according to claim 1, which comprises the acid in an amount that adjusts the pH value of the composition from 3 to 6.

7. A herbicidal composition according to claim 1, which comprises compound G in a ratio by weight with respect to compound A of from 50:1 to 20:1.

8. A method of controlling undesired plant growth in crops of useful plants, wherein a herbicidally effective amount of a composition according to claim 1 is applied on the crop plant or on the locus thereof.

9. A method according to claim 8, wherein the crop plant is maize or soybeans.

10. A method according to claim 8, wherein the crops of useful plants are treated with the composition at rates of application that correspond to a total amount of active ingredient of from 20 to 400 g per hectare.

11. A method of increasing the effectiveness of a herbicidal composition comprising, in addition to customary inert formulation adjuvants, as active ingredient a) a herbicidally effective amount of at least one compound G selected from the group of compounds of formula $G_1$ $$W-O-\text{C}_6H_4-O-\overset{CH_3}{\underset{*}{CH}}-COO-R_{10},\quad (G_1)$$

wherein $R_{10}$ is $C_1-C_4$alkyl, $CH_2C\equiv CH$ or $CH_2CH_2O-N=C(CH_3)_2$, W is a radical of the formula

[pyridine with $X_1$, $Y_1$ substituents], [chloroquinoxaline], or [chlorobenzoxazole]

wherein $X_1$ is hydrogen or F and
$Y_1$ is Cl or $CF_3$, and their D-enantiomers and agrochemically acceptable salts, and compounds of formula $G_2$ $$\quad (G_2)$$

[cyclohexenone structure with $R_{11}$, $R_{12}$, $R_{13}$, OH]

wherein $R_{11}$ is $CH_2CH_3$ or $-CH_2-CH=CH-Cl$ (trans),
$R_{12}$ is $CH_2CH_3$ or $CH_2CH_2CH_3$ and $R_{13}$ a radical of the formula

[tetrahydropyran], [tetrahydrothiopyran], or $H_3C-\overset{S-CH_2CH_3}{\underset{}{CH}}-CH_2-$, and their agrochemically acceptable salts, and b) an antagonistically active amount of at least one compound A selected from the group of compounds of formula $A_1$ $$U-SO_2-NH-CO-NH-\underset{R_2}{\overset{R_1}{\text{[pyrimidine/triazine ring with E]}}}\quad (A_1)$$

wherein $R_1$ is $CH_3$, $OCH_3$, $OCHF_2$ or Cl,
$R_2$ is $CH_3$, $OCH_3$, $OCHF_2$ or $CF_3$,
E is CH or N, and
U is a radical of the formula

[phenyl with $R_3$], [pyridine with $CO-N(CH_3)_2$ and methyl],

[thiophene with $COOCH_3$ and methyl] or [pyrrole with Cl, $COOCH_3$, methyl, $CH_3$]

wherein $R_3$ is $CH_2CH_2CF_3$, $CF_3$ or $COOR_4$, and
$R_4$ is $CH_3$, $CH_2CH_3$ or a radical of the formula

[oxetane], and their agrochemically acceptable salts, and compounds of formula $A_2$ $$\quad (A_2)$$

[pyridine with A, B, COOH, imidazolinone with $CH(CH_3)_2$, $CH_3$]

wherein

A is hydrogen,

B is $CH_2CH_3$ or $CH_2OCH_3$, or

A together with B forms a radical of the formula —CH=CH—CH=CH—, and their agrochemically acceptable salts, and compounds of formula $A_3$

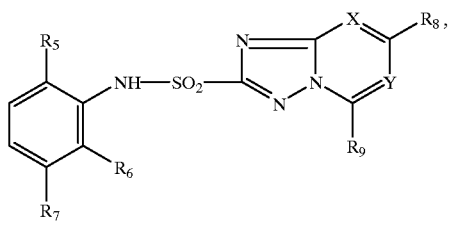

(A₃)

wherein $R_5$ is F, Cl or $COOCH_3$, $R_6$ is F or Cl, $R_7$ is hydrogen or $CH_3$, $R_8$ is $CH_3$, $OCH_3$ or F, $R_9$ is hydrogen, $OCH_3$ or $OCH_2CH_3$, and X and Y are each independently of the other CH or N, one of X and Y always being N, and their agrochemically acceptable salts, which method comprises adding to the composition an acid c) the pK value of which is smaller than the pK values of compounds G and A.

12. A herbicidal composition according to claim 6 wherein the pH value is 4–5.

13. A herbicidal composition according to claim 1 wherein component a) is oxasulfuron component b) is quizalofop-P and component c) is phthalic acid.

14. A herbicidal composition according to claim 1 wherein the compound of formula $G_1$ has the 2R configuration.

* * * * *